(12) United States Patent
Ma et al.

(10) Patent No.: US 11,054,623 B2
(45) Date of Patent: Jul. 6, 2021

(54) SURGICAL MICROSCOPE AND DEVICE FOR SWITCHING THE SAME AMONG MULTIPLE WORKING MODES

(71) Applicant: Carl Zeiss Meditec AG, Jena (DE)

(72) Inventors: Tao Ma, Shanghai (CN); Jian Jin, Shanghai (CN); Quanrong Gong, Shanghai (CN); Xiangxiang Zhang, Shanghai (CN)

(73) Assignee: Carl Zeiss Meditec AG, Jena (DE)

( * ) Notice: Subject to any disclaimer, the term of this patent is extended or adjusted under 35 U.S.C. 154(b) by 797 days.

(21) Appl. No.: 15/845,782

(22) Filed: Dec. 18, 2017

(65) Prior Publication Data

US 2018/0180865 A1    Jun. 28, 2018

(30) Foreign Application Priority Data

Dec. 23, 2016   (CN) .......................... 201611208161.5
Jan. 11, 2017   (CN) .......................... 201710019640.0
Jan. 11, 2017   (CN) .......................... 201720031205.5

(51) Int. Cl.
  *G02B 21/00*    (2006.01)
  *G02B 21/06*    (2006.01)
  (Continued)

(52) U.S. Cl.
  CPC ......... *G02B 21/0012* (2013.01); *G01D 5/145* (2013.01); *G01D 5/342* (2013.01);
  (Continued)

(58) Field of Classification Search
  CPC ........ G01D 5/145; G01D 5/342; A61C 19/00; G02B 21/0012; G02B 21/025;
  (Continued)

(56) References Cited

U.S. PATENT DOCUMENTS 6,650,357 B1 *  11/2003  Richardson ............... G01J 3/10
                                                              348/80
2005/0111233 A1 *  5/2005  Vezard .................... F21V 14/08
                                                             362/552
(Continued)

FOREIGN PATENT DOCUMENTS

DE      202007012433 U1    1/2009

OTHER PUBLICATIONS

KHK Stock Gears, Miter Gears, https://khkgears.net/new/miter_gears.html, available as of 2015, accessed Dec. 10, 2020 (Year: 2015).*

*Primary Examiner* — Derek S. Chapel
*Assistant Examiner* — Adam W Booher
(74) *Attorney, Agent, or Firm* — Walter Ottesen, P.A.

(57) ABSTRACT

The invention is directed to a surgical microscope and a device for switching the same among multiple working modes. The device includes an illumination rotary member and an observation rotary member that are arranged, respectively, in the illumination beam path and the observation beam path of the surgical microscope and are drivable by the same power source to rotate synchronously among multiple rotary positions corresponding to the multiple working modes. In each of the rotary positions, light from a light source of the surgical microscope passes through one or more of multiple light-through-portions of the illumination rotary member along the illumination beam path to illuminate the observed object, and then passes through one or more of multiple light-through-portions of the observation rotary member along the observation beam path to reach the eyepiece and/or an observation instrument of the surgical microscope.

39 Claims, 8 Drawing Sheets

(51) Int. Cl.
  G02B 5/30       (2006.01)
  G02B 21/02      (2006.01)
  G01D 5/14       (2006.01)
  G01D 5/34       (2006.01)
  G02B 21/24      (2006.01)
  G02B 21/22      (2006.01)
  G02B 30/34      (2020.01)
  G02B 21/16      (2006.01)
  A61B 90/20      (2016.01)
  A61C 19/00      (2006.01)

(52) U.S. Cl.
  CPC ......... *G02B 5/3025* (2013.01); *G02B 21/025* (2013.01); *G02B 21/06* (2013.01); *G02B 21/22* (2013.01); *G02B 21/248* (2013.01); *G02B 30/34* (2020.01); *A61B 90/20* (2016.02); *A61C 19/00* (2013.01); *G02B 21/16* (2013.01)

(58) Field of Classification Search
  CPC ...... G02B 21/06; G02B 21/22; G02B 21/248; G02B 21/16; G02B 21/0004; G02B 30/34; G02B 5/3025; G02B 5/20; A61B 90/20
  See application file for complete search history.

(56)  References Cited

U.S. PATENT DOCUMENTS

2007/0139619 A1\*  6/2007  DeCusatis ............ H04N 13/398
                                                353/7
  2012/0003627 A1\*  1/2012  Scholl .............. G01N 33/56983
                                                435/5
  2014/0291547 A1\* 10/2014  Lim ...................... G02B 21/16
                                                250/458.1

\* cited by examiner

FIG. 10

SURGICAL MICROSCOPE AND DEVICE FOR SWITCHING THE SAME AMONG MULTIPLE WORKING MODES

CROSS REFERENCE TO RELATED APPLICATION

This application claims priority of Chinese patent application no. 2016 11 208 161.5, filed Dec. 23, 2016, Chinese patent application no. 2017 10 019 640.0, filed Jan. 11, 2017, and Chinese Utility Model 2017 20 031 205.5, filed Jan. 11, 2017 and the entire content of the above applications is incorporated herein by reference.

FIELD OF THE INVENTION

The invention relates to a surgical microscope, and more specifically to a device for switching a surgical microscope among multiple working modes. The invention further relates to solutions of optical application of the surgical microscope.

BACKGROUND OF THE INVENTION

Filters are used in some surgical microscopes to select lights with different spectral characteristics, polarization states or phase properties, which lights are reflected, refracted, absorbed, diffused or manifest other optical properties differently in different media or media interfaces. As a result of this, the surgical microscope may have a plurality of different working modes to achieve different functions or uses.

Such kind of surgical microscope is usually equipped with at least two filters used separately or cooperatively with respect to an illumination beam path and an observation beam path of the surgical microscope. In prior art, when particular filters are to be used in a working mode, respective filters have to be manually moved into the illumination beam path or the observation beam path, and when the filters are required to be replaced in order to be switched to another working mode, the original filters must be manually moved out of the illumination beam path or the observation beam path again and then other filters are manually moved into the beam paths. Alternatively, each of the filters is equipped with a separately controlled motor, by means of which the corresponding filters are automatically controlled to move into or out of the illumination beam path or the observation beam path. For example, German patent DE202007012433U1 discloses means for respectively controlling two filters to move into and out of the illumination beam path and the observation beam path.

However, with the increasing of the functions of a surgical microscope, more and more filters need to be added therein. Manual and separate movement of the filters results in complex, time-consuming, troublesome and inaccurate operations. Automatic movement of the filters by motors requires the filters to be provided with more motors and associated cables, which leads to increase in size and weight of the surgical microscope as well as increased cost thereof.

An objective of the invention is therefore to address the above or other problems in the prior art.

SUMMARY OF THE INVENTION

The above objective of the invention can be achieved by the device and surgical microscope as stated hereinbelow.

According to the invention, a device for switching a surgical microscope among multiple working modes is provided, the device comprising an illumination rotary member and an observation rotary member that are arranged respectively in an illumination beam path and an observation beam path of the surgical microscope and are drivable by the same power source to rotate synchronously among multiple rotary positions corresponding to the multiple working modes, and in each of the rotary positions, light from a light source of the surgical microscope passes through one or more of multiple light-through-portions of the illumination rotary member along the illumination beam path to be irradiated onto an observed object, and then passes through one or more of multiple light-through-portions of the observation rotary member along the observation beam path to reach an eyepiece or an observation instrument of the surgical microscope.

According to a feature of the device, the illumination rotary member and the observation rotary member may be two discs which are provided with meshed teeth on respective peripheries to enable synchronous rotation.

According to a feature of the device, the light-through-portion of the illumination rotary member may include an illumination through-hole provided in the illumination rotary member or an illumination filter mounted in the illumination through-hole, and the light-through-portion of the observation rotary member may include an observation through-hole provided in the observation rotary member or an observation filter mounted in the observation through-hole.

According to a feature of the device, the power source may comprise a motor in drive coupling with the illumination rotary member or the observation rotary member, and/or a driving mechanism that can be operated manually and is in drive coupling with the illumination rotary member or the observation rotary member.

According to a feature of the device, the device may further comprise a sensor for detecting the rotary position of the illumination rotary member and/or the observation rotary member, wherein the motor is shut down or operation of the driving mechanism is stopped upon detection of a predetermined rotary position by the sensor.

According to a feature of the device, the sensor may be a Hall sensor, which detects the predetermined rotary position when being aligned with a magnet provided in the illumination rotary member or the observation rotary member.

According to a feature of the device, the sensor may be a light interrupter, which detects the predetermined rotary position when being aligned with a shade provided in the illumination rotary member or the observation rotary member.

According to a feature of the device, the device may further comprise a spring mechanism, and a plurality of grooves may be provided on the circumferential positions of the illumination rotary member or the observation rotary member, the spring mechanism including a protrusion biased against the circumferential positions of the illumination rotary member or the observation rotary member in a circumferentially immobile manner, which protrusion is engaged in a corresponding one of the grooves in each of the rotary positions.

The invention also provides a surgical microscope comprising a device as described above.

According to a feature of the surgical microscope, in one of the multiple rotary positions, the light-through-portion of the illumination rotary member through which light passes may be a hollow illumination through-hole, and the lightthrough-portion of the observation rotary member through which light passes may be an observation filter for caries detection.

According to a feature of the surgical microscope, the observation filter for caries detection has a transmission ratio between 20% and 35% for light with a wavelength of 500 nm to 550 nm; a transmission ratio of greater than 50%, preferably greater than 70%, and more preferably greater than 90% for light with a wavelength greater than a predetermined value between 600 nm and 650 nm, for example 620 nm; and a transmission ratio of less than 0.1%, preferably less than 0.01% for light with a wavelength of 380 nm to 430 nm.

According to a feature of the surgical microscope, in one of the multiple rotary positions, the light-through-portion of the illumination rotary member through which light passes may be a first polarizer as the illumination filter, and the light-through-portion of the observation rotary member through which light passes may be a second polarizer as the observation filter, the first and second polarizers having polarization directions intersecting with each other.

According to a feature of the surgical microscope, the polarization directions of the first and second polarizers may be perpendicular to each other.

According to a feature of the surgical microscope, in one of the multiple rotary positions, the light-through-portion of the illumination rotary member through which light passes may be an illumination filter for extending solidifying time of a teeth filling material, and the light-through-portion of the observation rotary member through which light passes may be a hollow observation through-hole.

According to a feature of the surgical microscope, the illumination filter for extending solidifying time of the teeth filling material has a transmission ratio of greater than 90% for light with a wavelength greater than a predetermined value between 500 nm and 600 nm, for example 550 nm.

According to a feature of the surgical microscope, in one of the multiple rotary positions, the light-through-portion of the illumination rotary member through which light passes may be an illumination filter for increasing contrast for blood observation, and the light-through-portion of the observation rotary member through which light passes may be a hollow observation through-hole.

According to a feature of the surgical microscope, in one of the multiple rotary positions, the light-through-portion of the observation rotary member through which light passes may be an observation filter for increasing contrast for blood observation, and the light-through-portion of the illumination rotary member through which light passes may be a hollow illumination through-hole.

According to a feature of the surgical microscope, the filter for increasing contrast for blood observation may be a green filter.

According to a feature of the surgical microscope, the filter for increasing contrast for blood observation has a higher transmission ratio for light with a wavelength between 500 nm and 550 nm, for example 525 nm, than that for light with other wavelengths, wherein a full width at half maximum is in between of +/−50 nm and +/−90 nm, preferably is +/−70 nm.

According to a feature of the surgical microscope, a light source with a central wavelength of between 500 nm and 550 nm, for example 525 nm, may be used in a working mode of increasing contrast for blood observation.

According to a feature of the surgical microscope, the observation filter for caries detection may be a filter that is able to pass red fluorescent light therethrough.

According to a feature of the surgical microscope, the illumination filter for extending solidifying time of a teeth filling material may be a filter that is able to filter out part or all of UV light and/or blue light.

According to a feature of the surgical microscope, the surgical microscope may further comprise a magnification changer disposed between the illumination rotary member and the observation rotary member, wherein light enters the observation beam path from the illumination beam path via the magnification changer.

According to a feature of the surgical microscope, the surgical microscope may be a dental surgical microscope.

In the surgical microscope and the device for switching the surgical microscope among multiple working modes according to the invention, a plurality of filters are arranged respectively on two or more rotary members which are driven by the same power source to rotate synchronously, so that when the surgical microscope is switched among different working modes, it is possible to control the respective filters, using a single power source, to accurately move into or out of the illumination beam path or the observation beam path, thereby easily realizing separate or cooperative use of the filters. In this way, it is possible to avoid the complex operations in the prior art to separately move each of the filters into or out of the beam paths during switching of working modes and to reduce the number of motors separately designated to each of the filters, and thus to save the internal space of the surgical microscope, reduce the volume and weight thereof, shorten operation time thereof and improve convenience in use, finally reducing cost and enhancing efficiency.

BRIEF DESCRIPTION OF THE DRAWINGS

The invention will now be described with reference to the drawings wherein.

DESCRIPTION OF THE PREFERRED EMBODIMENTS OF THE INVENTION

The surgical microscope and the device for switching the surgical microscope among multiple working modes according to embodiments of the invention will be illustrated below with reference to the drawings.

Figure 1:
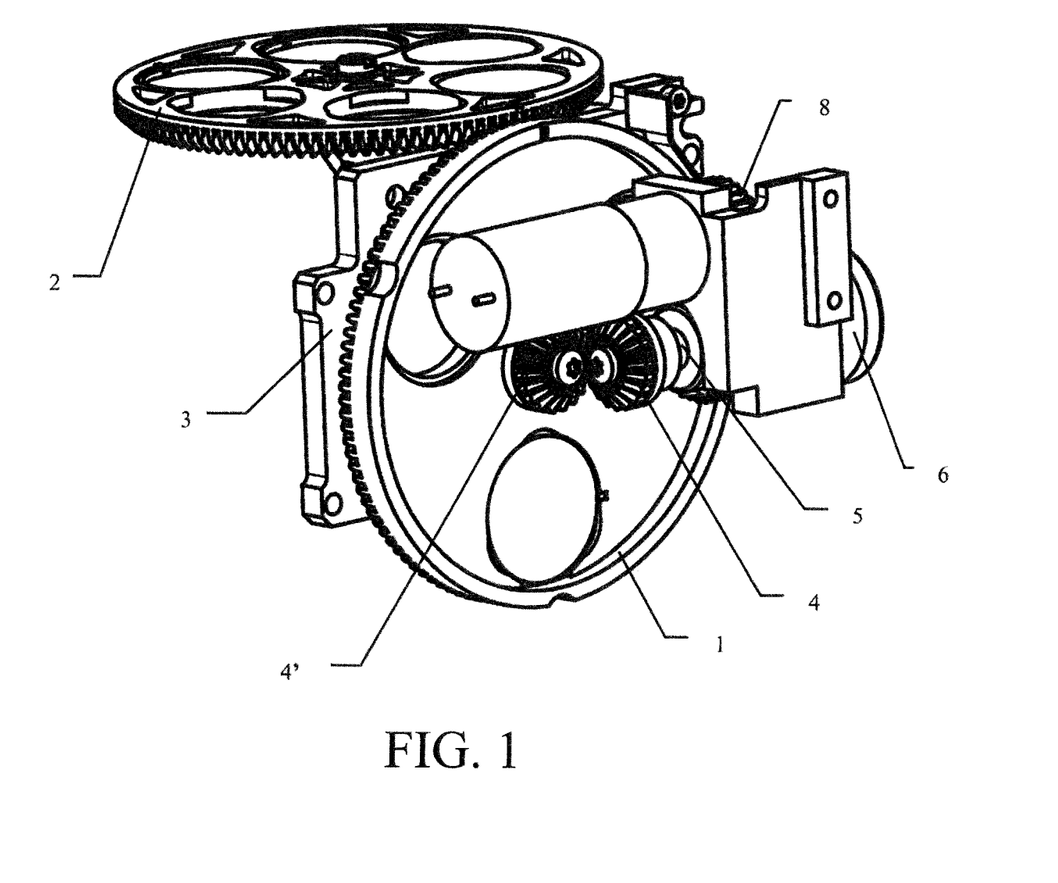
FIG. 1 is an assembled view of a device for switching the surgical microscope among multiple working modes according to one embodiment of the invention.
Figure 2:
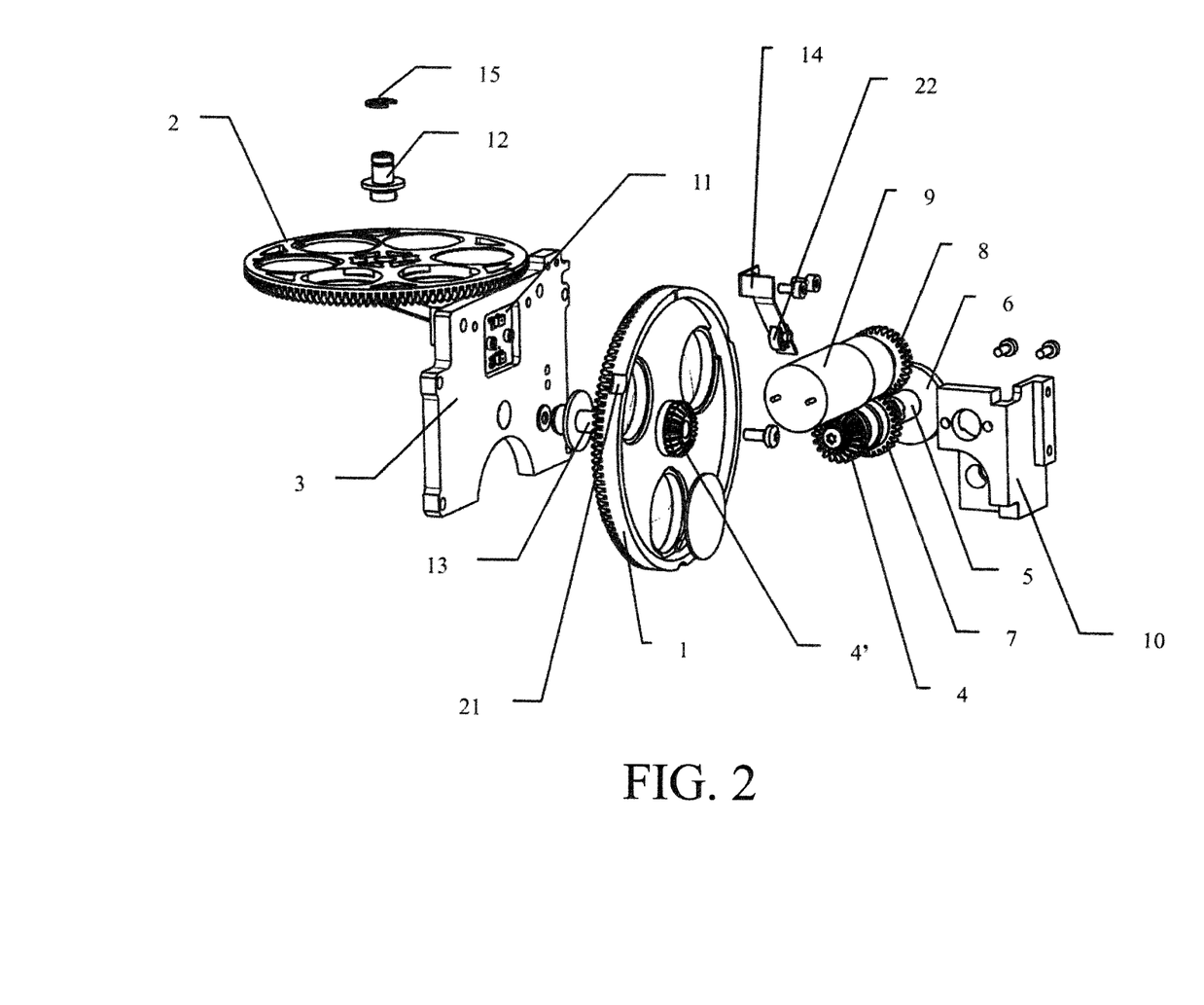
FIG. 2 is an exploded view of the device shown in FIG. 1.
Figure 3:
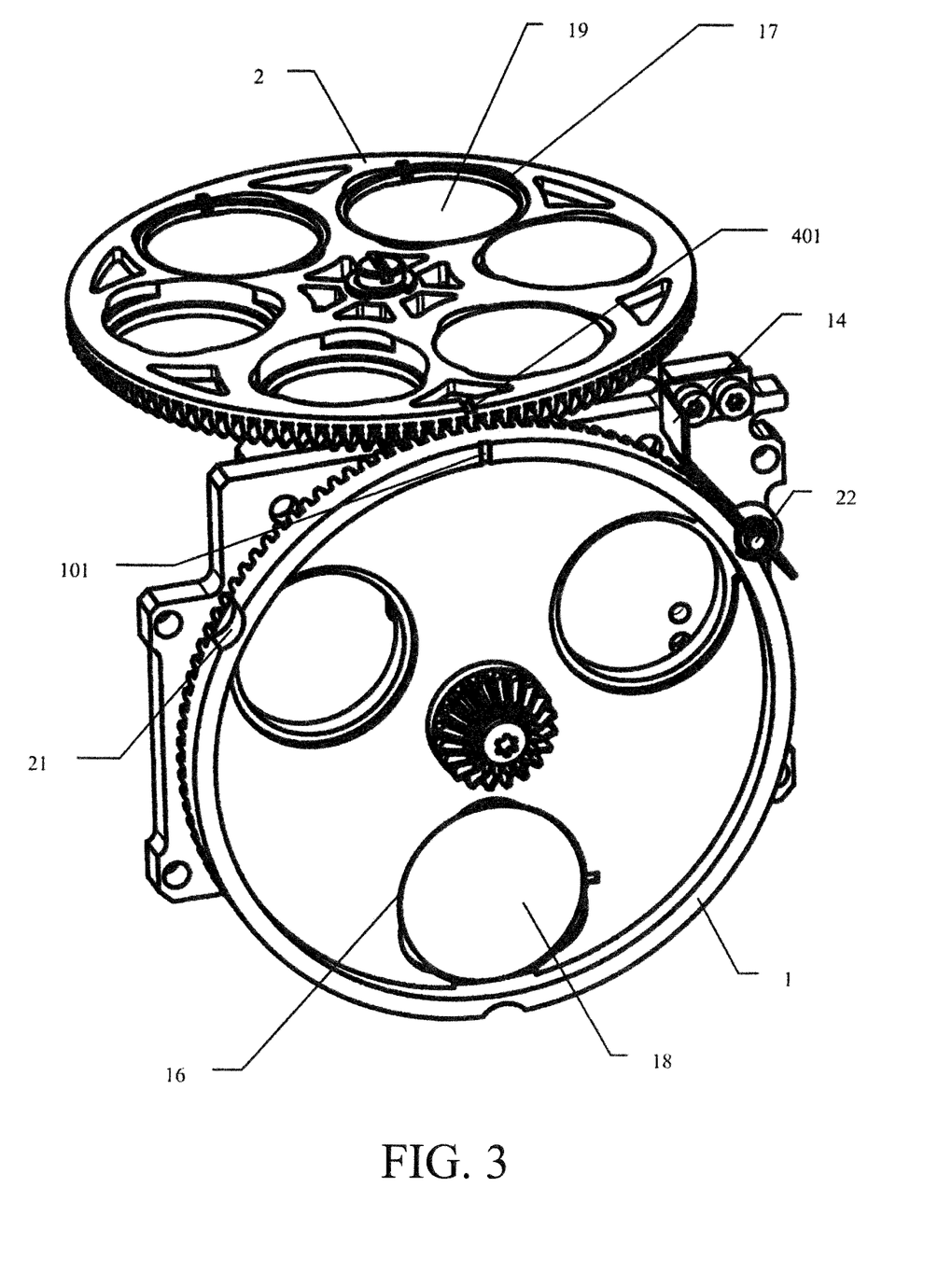
FIG. 3 is an assembled view of the device shown in FIG. 1 with some components thereof being omitted.

As shown in FIGS. 1 to 3, the device for switching the surgical microscope among multiple working modes according to an embodiment of the invention mainly includes two rotary members 1 and 2 arranged in an illumination beam path and an observation beam path, respectively. The two rotor members 1 and 2 are driven by the same power source to rotate synchronously among multiple rotary positions corresponding to the multiple working modes. The term "rotary position" in the invention refers to an angular position of the rotary member 1 and/or 2 in respective rotary directions (circumferential direction).

In the invention, the illumination beam path refers to a path traveled by a light that is emitted from a light source of the surgical microscope, passes a series of optical elements and is irradiated onto an observed object of the surgical microscope, and the observation beam path refers to a path traveled by a light that passes a series of optical elements after reflection by the observed object and then reaches an eyepiece of the surgical microscope (or a human eye, other image receiving means, an observation instrument such as a camera). For instance, in the exemplary diagram of beam paths of the surgical microscope shown in FIG. 8, the path indicated by the solid line is the illumination beam path, where the light is emitted from a light source 81 and travels until reaching an illumination plane 89 at which the observed object is placed, and the path indicated by the dotted line is the observation beam path, where the light travels up to an eyepiece 95 or a human eye 96 after being reflected from the illumination plane 89. In the exemplary mode of beam paths in the embodiment of the invention shown in FIG. 8, the illumination beam path extends substantially in a horizontal direction, while the observation beam path extends substantially in a vertical direction.

Figure 8:
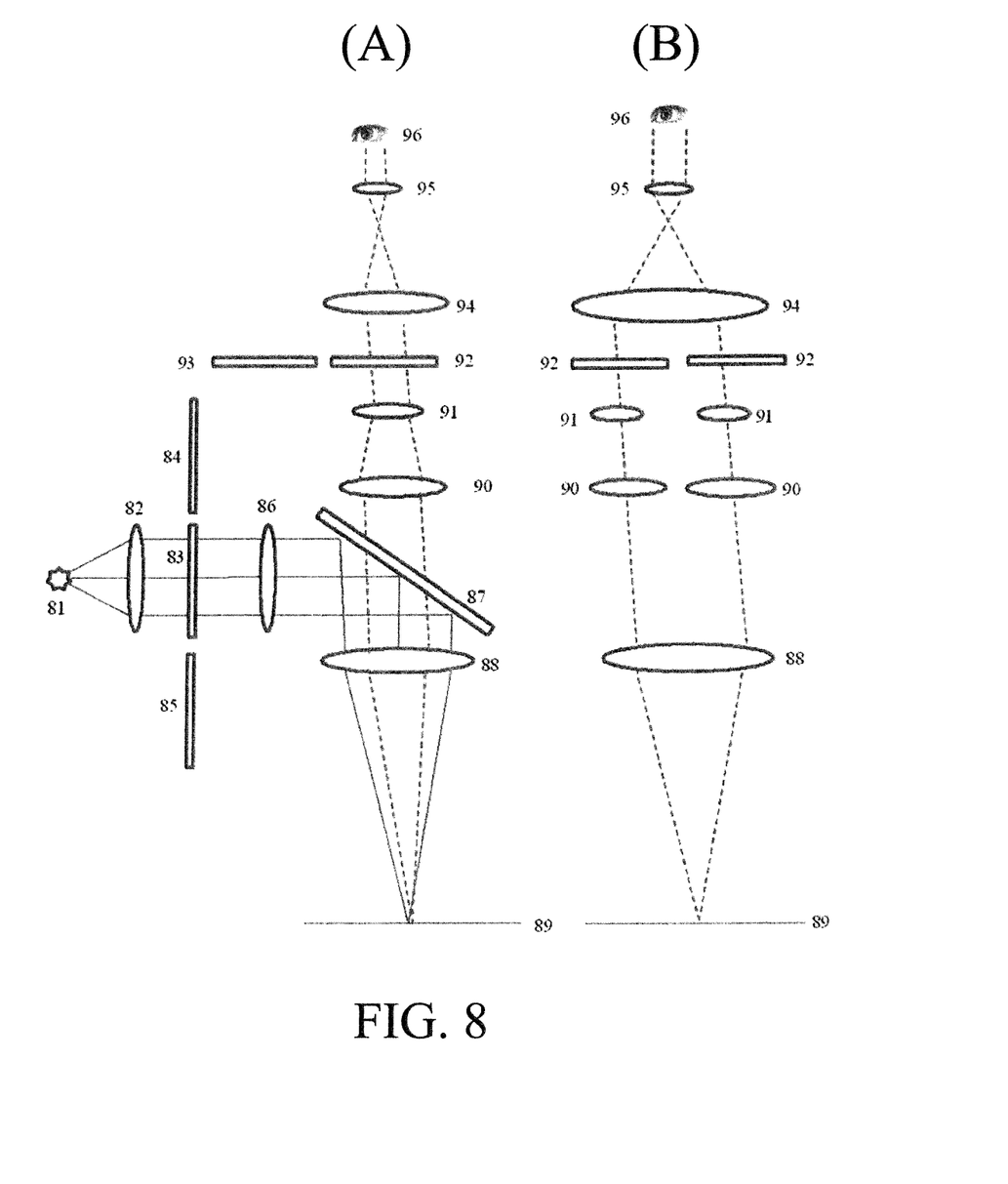
FIG. 8 shows beam paths of the surgical microscope according to the embodiment of FIG. 1.

Returning to FIGS. 1 to 3, the rotary member 1 is substantially vertically oriented and the rotary member 2 is substantially horizontally oriented, in order to be placed in the illumination beam path and the observation beam path, respectively, shown in FIG. 8. For easier differentiation, the rotary members 1 and 2 of the invention can be referred to as "illumination rotary member 1" and "observation rotary member 2", respectively. In the illustrated embodiment, the illumination rotary member 1 and the observation rotary member 2 are configured to have a shape of a disc (circular plate, wheel) and are provided with meshed teeth (for example, gear teeth with a beveled angle of 45°) on their respective peripheries so as to achieve synchronous rotation between the two rotary members. In other words, rotation of any one of the illumination rotary member 1 and the observation rotary member 2 caused by driving of a single power source will drive the other one to rotate synchronously therewith.

It should be noted that the drive for synchronously rotating the illumination rotary member and the observation rotary member is not limited to the meshed teeth as described above, and may include any other suitable means that are conceivable by those skilled in the art, for example screw drive, belt drive, chain drive, cam drive, ratchet drive and the like arranged between two rotary members to achieve the synchronous rotation thereof. In addition, the positions and orientations of the illumination rotary member 1, the observation rotary member 2, the illumination beam path and the observation beam path are not limited to the horizontal and vertical directions described and shown in the embodiment of the invention, and may include any other suitable means that can be conceived by those skilled in the art to allow the light to pass the relevant rotary members.

As illustrated by FIGS. 1 and 2, the illumination rotary member 1 is mounted on a rotary shaft 13 thereof by means of, for example, a screw and a flat washer, and the observation rotary member 2 is mounted on a rotary shaft 12 thereof by means of, for example, a snap ring 15, and then the rotary shafts 12 and 13 are both secured to a bracket 3. In the illustrated embodiment, the illumination rotary member 1 is configured to be driven by a power source which may include for example a motor 9 in drive coupling with the illumination rotary member 1. The motor 9 is mounted to a motor base 10 on which a drive rotary shaft 5 is secured. A spur gear 8 is fixedly mounted on an output shaft of the motor 9, and the spur gear 7 meshed with the spur gear 8, is fixedly mounted on the drive rotary shaft 5. A bevel pinion 4 with a beveled angle of, for example, 45° is fixedly mounted at a tip end of the drive rotary shaft 5, and the bevel pinion 4 is meshed with a bevel pinion 4' fixedly arranged at the center of the illumination rotary member 1 and/or at an end of the rotary shaft 13. Accordingly, a rotary power of the motor 9 is transferred to the drive rotary shaft 5 via the meshed spur gears 7, 8, and then to the illumination rotary member 1 via the meshed bevel gears 4, 4' from the drive rotary shaft 5, so as to drive the illumination rotary member 1 in rotation which, in turn, drives the observation rotary member 2 to rotate synchronously. Here, a desired reduction ratio from the motor 9 to the illumination rotary member 1 can be achieved by setting the ratio of teeth numbers of the spur gears 7, 8 and/or the ratio of teeth numbers of the bevel pinions 4, 4'. The drive coupling between the motor 9 and the illumination rotary member 1 is not limited to the above drive means using spur gears and bevel pinions, and may include for example screw drive, belt drive, chain drive and so on. As an alternative or additional means of the motor 9, the power source may also include a hand-coin wheel 6 that can be operated manually and in drive coupling with the illumination rotary member 1. Specifically, the hand-coin wheel 6 may be fixedly connected with the drive rotary shaft 5 via for example, a screw, and the manual rotation is transferred to the illumination rotary member 1 and the observation rotary member 2 via the drive rotary shaft 5. Of course, it is conceivable by those skilled in the art that the power source is not limited to the motor and hand-coin wheel, and may include any suitable means that is capable of providing power and in drive coupling with the rotary member 1 or 2, such as an air cylinder, an electromagnet and so on.

In the invention, the illumination rotary member 1 and the observation rotary member 2 are synchronously rotated among multiple rotary positions, and in each of the rotary positions, light from the light source of the surgical microscope passes through one of multiple light-through-portions of the illumination rotary member 1 along the illumination beam path and then illuminates the observed object, and further reaches an eyepiece of the surgical microscope after passing through one or more of multiple light-through-portions of the observation rotary member 2 along the observation beam path. The light-through-portions of the two rotary members 1 and 2 may include the through-holes provided therein and the filters mounted in the through-holes, wherein in some optical applications the through-hole may be hollow without any filter. In the invention, the through-holes and the filters in the illumination rotary member 1 may be referred to as an "illumination through-hole" and an "illumination filter", and the through-holes and the filters in the observation rotary member 2 may be referred to as an "observation through-hole" and an "observation filter".

In the present embodiment, as shown in FIG. 3, the number of the illumination through-holes 16 may be equal to the number of the rotary positions of the illumination rotary member 1 and the observation rotary member 2, and the number of the observation through-holes 17 may be twice the number of the illumination through-holes. This is because the light of the observation beam path will be divided into two branches (see part (B) of FIG. 8 and the related illustration) to configure the surgical microscope of the present embodiment as a stereomicroscope (stereoscopic microscope) to allow a viewer to observe a stereo-image with both eyes. According to the synchronously rotational relationship between the illumination rotary member 1 and the observation rotary member 2 as stated above, the two rotary members have mutually corresponding rotary positions. In other words, each rotary position of the illumination rotary member 1 includes only one through-hole, while each rotary position of the observation rotary member 2 includes two through-holes corresponding thereto. In the illustrated embodiment, three illumination through-holes 16 and corresponding six observation through-holes 17 are provided, in which illumination filters 18 and observation filters 19 are selectively mounted or which are hollow without any filters depending on the working mode of the surgical microscope. It should be noted that the surgical microscope of the invention is not limited to the stereomicroscope and thus the relationship of correspondence between the through-holes and filters arranged on the illumination rotary member 1 and those on the observation rotary member 2 in each rotary position is not limited to one-to-two as depicted in the embodiment, but instead may include any other suitable relationship that can be derived by those skilled in the art.

In the illustrated embodiment, the light-through-portions of the two rotary members 1 and 2 may be for example, distributed uniformly along their respective circumferences. In order to ensure that in each rotary position the respective selected light-through-portions (through-holes or filters) of the rotary members 1 and 2 are located exactly at the correct positions in the illumination beam path and the observation beam path, respectively, it is necessary to ensure that the rotary members 1 and 2 are mounted in the correct circumferential positions relative to each other. In order for this, as shown in FIG. 3, slots 101 and 401 may be provided in outer peripheries of the rotary members 1 and 2 respectively according to the correct relative circumferential positions therebetween so that the correct mounting positions can be ensured as long as the slots 101 and 401 are aligned with each other when the rotary members 1 and 2 are mounted.

Meanwhile, in order for normal operation of the surgical microscope in different working modes, the illumination rotary member 1 and the observation rotary member 2 must be controlled in such a manner that they are stopped after rotating exactly to each corresponding rotary position. In order for this to occur, a sensor for detecting the rotary position of the rotary members 1 and 2 is provided such that the motor 9 can be switched off or operation of the hand-coin wheel 6 can be stopped when the sensor detects a desired predetermined rotary position.

Figure 4:
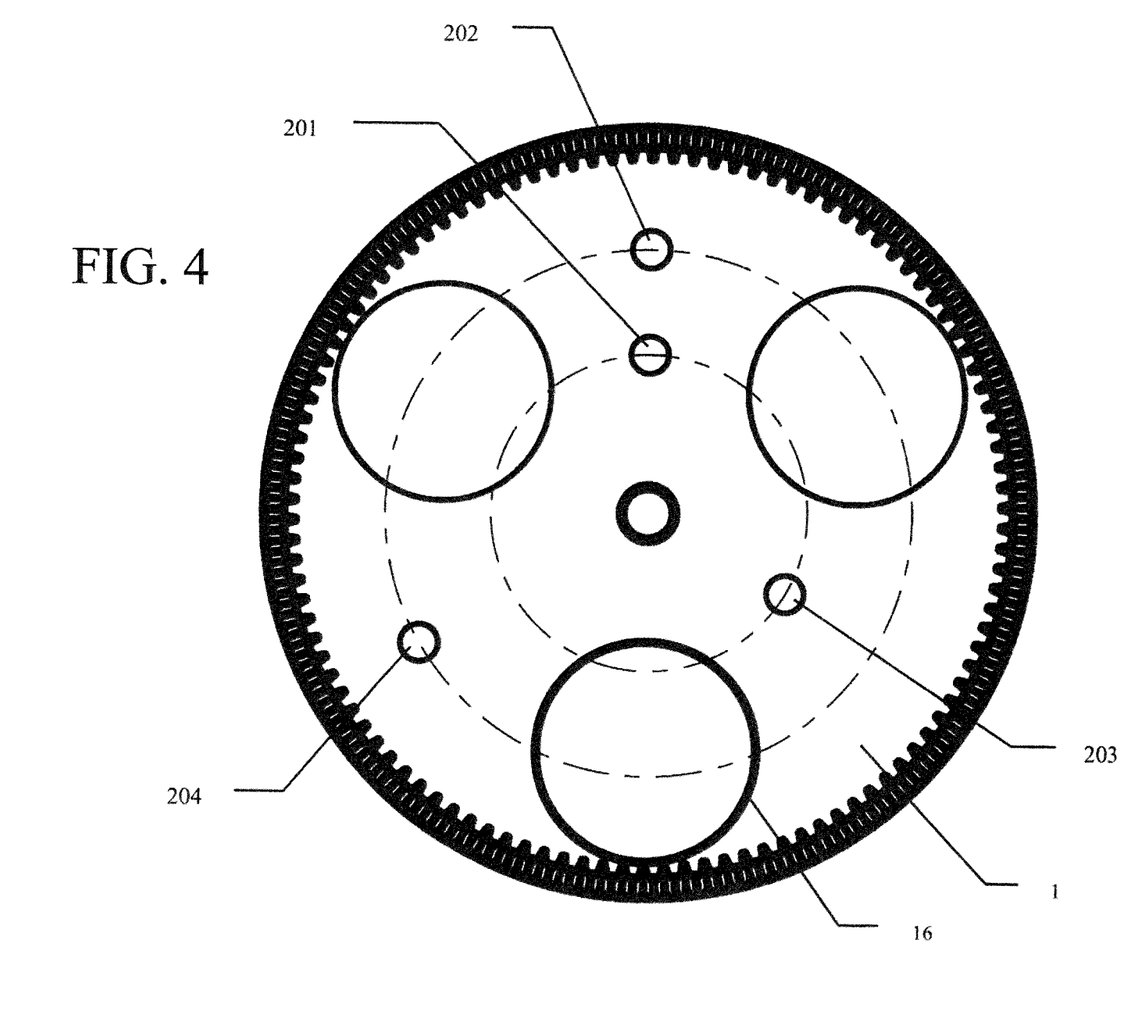
FIG. 4 schematically shows positions of the sensors for detecting the rotary position of a rotary member in the device shown in FIG. 1.

In the embodiment shown in FIG. 4, the Hall sensors are used to detect the rotary position. Specifically, as illustrated in FIG. 2, the bracket 3 may be provided with a positioning sensor PCB 11 in which two Hall sensors A and B are arranged vertically. On a surface of the illumination rotary member 1 that faces the bracket 3, as shown in FIG. 4, four magnets 201 to 204 are disposed which are divided into three groups arranged along a circumferential direction of the illumination rotary member 1 and corresponding to three rotary positions, respectively. The first group is comprised of two magnets 201, 202 arranged in a radial direction of the illumination rotary member 1 and positioned radially to align with the two Hall sensors, respectively, to determine that the illumination rotary member 1 is in a first rotary position. The second group is comprised of a single magnet 203 located at the same radial position as the magnet 201 of the first group at a radially inner side. The third group is comprised of a single magnet 204 located at the same radial position as the magnet 202 of the first group at a radially outer side. Any one of the magnets, when being aligned with a corresponding Hall sensor, will be detected by the Hall sensor to trigger a detection signal. The two Hall sensors thus can determine the rotary position of the illumination rotary member 1 according to the number and the radial position of the detected magnet, and then control or instruct whether rotation of the illumination rotary member 1 should be stopped or not.

Figure 9:
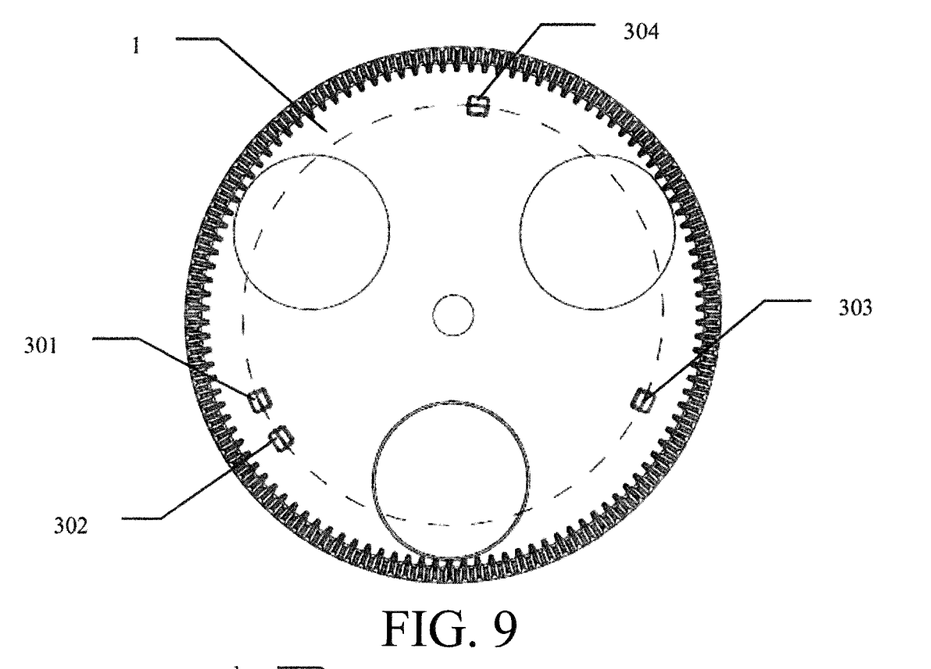
FIG. 9 schematically shows positions of the shades for detecting the rotary position of the rotary member in another embodiment of the invention; and, FIG. 10 is a top view of the rotary member with the shades in the embodiment of FIG. 9.
Figure 10:
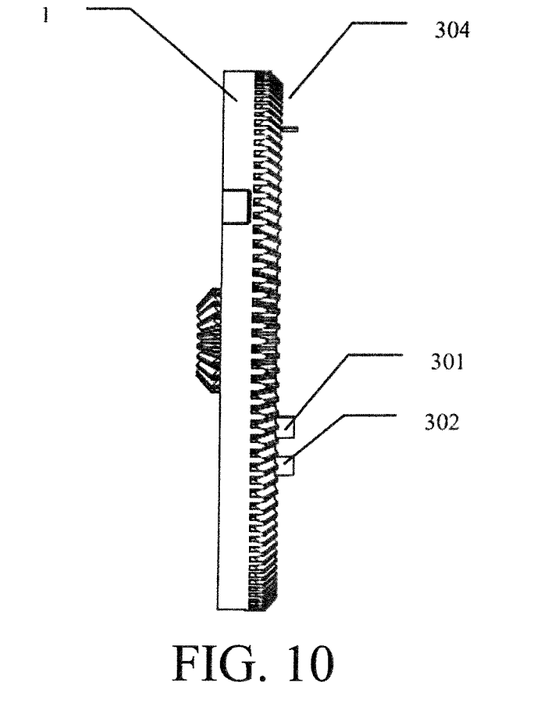

In another embodiment of the invention, the light interrupters (optical chopper) are used to detect the rotary position. Specifically, the bracket 3 may be provided with the sensor PCB 11 in which two light interrupters A and B are arranged horizontally. Also, as shown in FIGS. 9 and 10, the illumination rotary member 1 is provided with four shades 301 to 304 protruding towards the bracket 3. In a clearance of the illumination rotary member 1 facing the bracket 3, when the illumination rotary member 1 is rotated to a certain position where the shade thereon is aligned with a corresponding light interrupter, the shade is inserted between a light emitting assembly and a light receiving assembly of the light interrupter, so that the shade will be detected by the light interrupter to trigger a detection signal. The four shades 301 to 304 are divided into three groups arranged along a circumferential direction of the illumination rotary member 1 and corresponding to three rotary positions, respectively. The first group is comprised of two shades 301, 302 arranged in the circumferential direction of the illumination rotary member 1 and positioned circumferentially to align with and to shade the two corresponding light interrupters, thereby determining that the illumination rotary member 1 is in a first rotary position. The second group is comprised of only one shade 303 which shades the left light interrupter in a second rotary position but leaves the right light interrupter open to determine that the illumination rotary member 1 is in the second rotary position. The third group is also comprised of only one shade 304 which shades the right light interrupter in a third rotary position but leaves the left light interrupter open to determine that the illumination rotary member 1 is in the third rotary position. When power is on, the illumination rotary member 1 is reset by rotating to the first rotary position. Subsequently, during rotation of the illumination rotary member 1, it is determined whether the illumination rotary member 1 is rotated to the second rotary position or the third rotary position depending on the position and number of the detected shade to control or instruct whether rotation of the illumination rotary member 1 should be stopped or not.

Of course, those skilled in the art can appreciate that, apart from the above described Hall sensors and light interrupters, the invention may employ any other suitable sensors capable of detecting the angular position of a rotary object.

In order to stop the rotary members 1 and 2 in a desired rotary position, a spring mechanism, for example, a reed 14 shown in FIGS. 2 and 3 may be provided, and correspondingly a plurality of grooves 21 in the shape of, for example, an arc are arranged in a periphery of the illumination rotary member 1. The reed 14 may include a protrusion 22 biased against the periphery in a circumferentially immobile manner. In each rotary position, the protrusion 22 which is also in the shape of, for example, an arc is pressed by the reed 14 to engage in a corresponding groove 21, such that the rotary members 1 and 2 will be stopped in their current rotary positions once the rotational power applied thereto is withdrawn. Of course, if the rotary members 1 and 2 are driven continuously, it is necessary to apply a greater drive force to overcome the spring force of the reed 14 in order to allow the protrusion 22 to disengage from the groove 21 and to allow the rotary members 1 and 2 to rotate continuously. When the rotary position of the two rotary members 1 and 2 is changed manually using the hand-coin wheel 6 to switch the working mode of the surgical microscope, engagement between the protrusion 22 and the groove 21 can provide the operator with proper tactile feedback to indicate the entry into a rotary position or a working mode.

The following is a depiction of the operation of the surgical microscope and the device for switching the same among multiple working modes according to the illustrated embodiments. First of all, corresponding filters are selectively mounted in the illumination through-holes and/or the observation through-holes of the illumination rotary member 1 and/or the observation rotary member 2 in accordance with requirements of different working modes, wherein the filters may be used solely or cooperatively with respect to the illumination beam path and the observation beam path of the surgical microscope. When the surgical microscope is to be switched to a desired working mode, the operator may, for example, press a particular button (corresponding to the desired working mode) on a control panel of the surgical microscope to send an instruction to the motor 9 which therefore starts operation and drives the two rotary members 1 and 2 to rotate. During the rotation, the two Hall sensors or light interrupters keep detecting the rotary position of the rotary members 1 and 2. When the rotary members are rotated to the rotary position corresponding to the desired working mode, corresponding sensors are triggered to send a signal to control the motor 9 to stop rotation, and at this time, the protrusion 22 on the spring mechanism is exactly engaged in the corresponding groove 21 to stop the rotary members 1 and 2 in the desired rotary position so as to enter the desired working mode. Alternatively, the operator may select the desired working mode by operating the hand-coin wheel 6. When rotation of the hand-coin wheel 6 drives the rotary members 1 and 2 to reach a certain rotary position, the sensor detects this rotary position and sends a signal, to show the operator on the panel of the surgical microscope the working mode corresponding to current rotary position. If the working mode is not a desired one, the operator continues to operate the hand-coin wheel 6 to rotate to a next rotary position until the desired working mode is arrived at.

In the illustrated embodiment, each of the two rotary members 1 and 2 includes at least three light-through-portions. Therefore, for example, three working modes can be set for the surgical microscope as illustrated in Table 1, in which "1" means a corresponding magnet or shade is detected by the sensor A or B, and "0" means no magnet or shade is detected.

TABLE 1

| Sensor signal | | | Type of the filter on the illumination rotary member 1 (illumination beam path) | Type of the filter on the observation rotary member 2 (observation beam path) | Rotary position |
|---|---|---|---|---|---|
| Sensor A | Sensor B | Working mode | | | |
| 1 | 1 | Normal mode | None | None | First |
| 1 | 0 | Polarization mode | First polarizer | Second polarizer | Second |
| 0 | 1 | Fluorescence mode (caries detection mode) | None | Filter for caries detection | Third |

The above multiple working modes of the surgical microscope of the invention will be described below in conjunction with the exemplary beam paths of the surgical microscope shown in FIG. 8, in which part (A) shows both the illumination beam path and the observation beam path of the microscope, and part (B) shows only the observation beam path of a stereomicroscope that includes two branches of light for observation by both eyes.

(1) Polarization Mode

Polarization mode is set for an observation sample that may result in mirror reflection. For example, when the surgical microscope is used in dental treatment and diagnosis to observe teeth, mirror reflection (direct reflection) will be generated on teeth glaze and saliva on the teeth. With illumination of reflected light, the incident light struck onto the teeth can be directly received by human eyes or a camera after being subject to mirror reflection so that bright spots will be observed. The light reflected by teeth includes, besides light from mirror reflection, lots of light from diffuse reflection that has vibration in all directions. If the vibration directions of the illumination light are changed into one direction by a linear polarizer and the mirror reflection light in this one direction is cut off by another polarizer while allowing the passage of light from diffuse reflection in the other directions, the bright spots received by human eyes or the camera will be reduced, and meanwhile details on the teeth can be observed by diffuse reflection imaging.

In the polarization mode, as shown in part (A) of FIG. 8, a first polarizer 83 mounted in the illumination through-hole in the illumination rotary member 1 and a second polarizer 92 mounted in the observation through-hole in the observation rotary member 2 are simultaneously rotated into the illumination beam path and the observation beam path, respectively. The light emitted from a light source 81 is an ordinary illumination light, which is irradiated onto an illumination plane 89, at which an observed object is placed, through an illumination lens 82, the first polarizer 83, an illumination lens 86, a reflective mirror 87 and an objective lens 88. The light irradiated onto the illumination plane 89 after passing through the first polarizer 83 is changed into a polarized light with only one vibration direction. Then, the lights reflected by the observed object on the illumination plane 89 include both the polarized reflected light from mirror reflection and diffuse light from diffuse reflection which simultaneously pass through the objective lens 88, the reflective mirror 87, a first lens 90 for a magnification changer, a second lens 91 for a magnification changer and the second polarizer 92. The first polarizer 83 and the second polarizer 92 are arranged in corresponding through-holes in such a manner that their polarization directions are perpendicular to each other, as a result of which, the light from mirror reflection is cut off by the second polarizer 92, while part of the light from diffuse reflection that has a vibration direction parallel with the polarization direction of the second polarizer 92 is allowed to continuously pass through a tube lens 94 and an eyepiece 95 to be observed by a human eye 96, so that the human eye will not see bright spots generated by mirror reflection. The first and second polarizers have an extinguishing ratio greater than 800:1 at a wavelength of, for example, 550 nm to ensure complete removal of the bright spots. In addition, the polarization directions of the first and second polarizers may be configured to be adjustable relative to each other, and it will suffice that they intersect with each other without having to be exactly perpendicular to each other. In this case, the extinguishing ratio can be adjusted (because only part of the light from mirror reflection is cut off by the second polarizer 92) to observe the changes of the observed object at different angles.

(2) Caries Detection Mode (Fluorescence Mode)

The fluorescence mode may be used for example in dental treatment and diagnosis to detect carious teeth. When a tooth is carious, it will generate a special purine, which can emit red fluorescence when irradiated by a light with a wavelength of 405 nm. By using this characteristic of a carious tooth, the fluorescence mode is set in such a manner that the tooth is irradiated by a fluorescence with a wavelength of 405 nm and then red fluorescence is filtered by a particular filter to allow the human eye or camera to observe and identify the carious tooth clearly.

Figure 5:
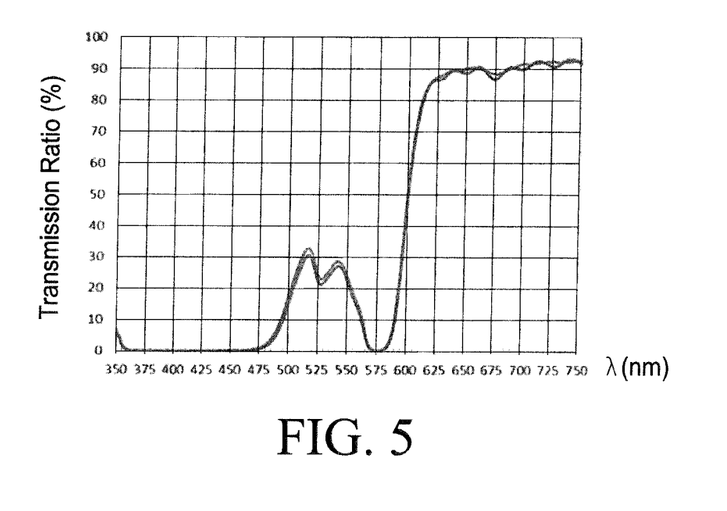
FIGS. 5 to 7 show spectrograms of the surgical microscope of the invention in a caries detection working mode, a prolong curing time working mode and a blood observation working mode, respectively.

At the time of switching to the fluorescence mode, a hollow illumination through-hole (a through-hole without any filters) in the illumination rotary member 1 and a filter 93 for caries detection mounted in the observation through-hole in the observation rotary member 2 are rotated simultaneously into the illumination beam path and the observation beam path, respectively. At the same time the first and second polarizers in the above polarization mode naturally are moved automatically out of the illumination beam path and the observation beam path along with rotation of the rotary members 1 and 2. In the fluorescence mode, the light source emits a violet light with a wavelength of 405 nm, which is irradiated onto the illumination plane 89 after passing through the illumination lens 82, the illumination through-hole in the illumination rotary member 1, the illumination lens 86, the reflective mirror 87 and the objective lens 88. If a carious tooth is irradiated, the part with caries will generate red fluorescent light which can be observed by the human eye 96 or the camera after passing through the objective lens 88, the reflective mirror 87, the first lens 90 for magnification changer, the second lens 91 for a magnification changer, the filter 93, the tube lens 94 and the eyepiece 95. Other parts of the teeth will not generate red fluorescent light, which allows clear identification of the carious tooth. The filter 93 in this working mode will filter out the violet light with a wavelength of 405 nm while letting the red fluorescent light pass. Optimized spectrum distribution allows the human eye to observe an image of carious teeth with better contrast. For example, the spectrum data of the filter in this working mode may be selected as shown in FIG. 5: a transmission ratio between 20% and 35% for light with a wavelength of 500 nm to 550 nm; a transmission ratio of greater than 50%, preferably greater than 70%, and more preferably greater than 90% for light with a wavelength greater than a predetermined value between 600 nm and 650 nm (for example 620 nm); and a transmission ratio of less than 0.1%, preferably less than 0.01% for light with a wavelength of 380 nm to 430 nm, wherein the transmission ratio at the wavelengths of 500 nm and 550 nm is so required to enhance contrast between carious teeth and ordinary teeth.

(3) Normal Mode

In normal mode, a hollow illumination through-hole (a through-hole without any filters) in the illumination rotary member 1 and a hollow observation through-hole (a through-hole without any filters as well) in the observation rotary member 2 are rotated simultaneously into the illumination beam path and the observation beam path, respectively. At this time, the filters used in other modes naturally are moved automatically out of the illumination beam path and the observation beam path along with rotation of the rotary members 1 and 2. An ordinary observation can be done by means of the surgical microscope in the normal mode.

In addition to the three modes listed in Table 1, more working modes can be achieved by increasing the number of the light-through-portions (for example, the through-holes and corresponding filters) in the rotary members 1 and 2 or replacing the filters in the through-holes of the illustrated embodiments with other filters, such as the prolong curing time mode and blood observation mode set forth below.

(4) Prolong Curing Time Mode

The filters used in the prolong curing time mode are set to extend the solidifying time of dental filling materials in dental treatment. Normal dental filling material will solidify more quickly under UV irradiation or blue light. If a filter is used to filter out UV light and part or whole of the blue light, the solidifying time can be prolonged to give the dentist more time to modify and shape the teeth.

Figure 6:
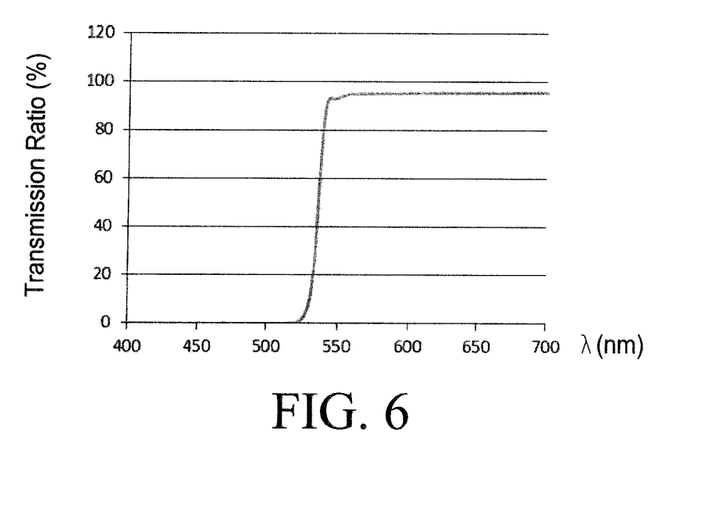

As shown in part (A) of FIG. 8, a filter 84 can be added into the illumination through-hole in the illumination rotary member 1, while the corresponding through-hole in the observation rotary member 2 is hollow, that is, without any filters. Alternatively, the filter 84 can be provided directly behind the light source 81. Thus, the light emitted from the light source and being filtered by the filter contains less UV light and/or blue light, and therefore the light irradiated onto the observed teeth contains less UV light and/or blue light, which can prolong the solidifying time of dental filling materials. A spectrum curve of the filter in this working mode may be set as shown in FIG. 6: a transmission ratio of greater than 90% for light with a wavelength A greater than a predetermined value between 500 nm and 600 nm (for example 550 nm).

In addition, the light that is irradiated to the observed teeth and contains less UV light and/or blue light can also be generated by a light source conforming to the above-mentioned spectrum characteristics.

(5) Blood Observation Mode

The blood observation mode can be used to increase contrast for blood observation. Red blood looks black under green light, while the color of other parts looks gray, so that blood and other parts can be distinguished more clearly.

Figure 7:
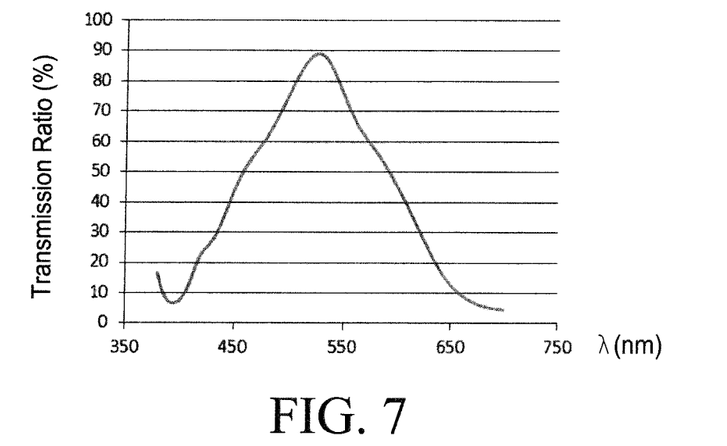

The blood observation mode can be realized by either a green filter or directly a green light source. A green filter 85, if used, can be added into the illumination through-hole of the illumination rotary member 1 while the corresponding through-hole in the observation rotary member 2 is hollow, that is, without any filters; or the green filter 85 can be added into the observation through-hole of the observation rotary member 2 while the corresponding through-hole in the illumination rotary member 1 is hollow, that is, without any filters; or the green filter 85 may be provided directly behind the light source 81. The spectrum curve of the green filter can be set as shown in FIG. 7, which has a higher transmission ratio for light with a wavelength A between 500 nm and 550 nm (for example 525 nm) than that of the light with other wavelengths, wherein a full width at half maximum (FWHM) is in between of +/−50 nm and +/−90 nm, preferably +/−70 nm. If a green light source is used to realize the green light mode, an LED green light source with a central wavelength of between 500 nm and 550 nm (for example 525 nm) can be selected, wherein it will suffice that the FWHM is less than 90 nm, preferably less than 70 nm.

According to the various working modes as described above, the surgical microscope of the invention apparently can be used as a dental surgical microscope to examine carious teeth, prolong the solidifying time of dental filling materials (curing time) and so on. Of course, depending on the function of the filters used, the surgical microscope of the invention may have other applications in other fields.

In the illustrated embodiments, there are merely one illumination rotary member and one observation rotary member arranged respectively in the illumination beam path and the observation beam path, but the invention is not limited to this. More than one illumination rotary member and/or more than one observation rotary member can be contemplated as long as they are arranged to rotate synchronously. In this case, the light in the illumination beam path and/or the observation beam path may be subject to twice or more filtering treatments as needed by corresponding filters in the illumination rotary member or the observation rotary member, so as to meet more complicated or more precise functional requirements. Also, the invention is not limited to the configuration shown in FIG. 3 in which three illumination through-holes 16 correspond to three rotary positions and six observation through-holes 17, but those skilled in the art can set less or more rotary positions and through-holes according to real requirements of product application. Likewise, the invention is not limited to the five types of filters as depicted above, and those skilled in the art may arrange other filters and light sources to meet special optical characteristics according to real requirements of product application.

Various modifications and variations may be made without departing from the scope of the invention through the exercise of those skilled in the art. According to practice of the disclosure of the invention, other embodiments of the invention are obvious for those skilled in the art.

It is understood that the foregoing description is that of the preferred embodiments of the invention and that various changes and modifications may be made thereto without departing from the spirit and scope of the invention as defined in the appended claims.

What is claimed is:

1. A device for switching a surgical microscope into and out of multiple working modes, the surgical microscope defining an observation beam path and having a light source defining an illumination beam path for irradiating an object viewable via said observation beam path, said surgical microscope further having an eyepiece or observation instrument arranged in said observation beam path, said device comprising:

an observation rotary member defining a first rotational axis and being arranged in said observation beam path;

an illumination rotary member defining a second rotational axis transverse to said first rotational axis and being arranged in said illumination beam path;

a gear assembly connecting said rotary members directly to each other so as to permit said rotary members to rotate synchronously among a plurality of rotary positions corresponding to respective ones of said working modes;

said illumination rotary member having a plurality of first light-through-portions for passing light at each of said rotary positions from said light source through one or more of said first light-through-portions along said illumination beam path to irradiate onto said object; and, said observation rotary member having a plurality of second light-through-portions for passing said light irradiated on said object along said observation beam path through one or more of said second light-through-portions to arrive at said eyepiece or observation instrument.

2. The device of claim 1, wherein said illumination rotary member and said observation rotary member are respective discs having respective peripheries; and, said gear assembly includes said discs being configured to have respective sets of teeth on corresponding ones of said peripheries; and, said sets of teeth are mutually meshed to permit the synchronous rotation thereof.

3. The device of claim 2, wherein said first-light-through portions include an illumination-through-hole or said illumination-through-hole with an illumination filter mounted therein; and, said second light-through-portions include an observation-through-hole or said observation-through-hole with an observation filter mounted therein.

4. The device of claim 3, wherein said device further comprises a spring mechanism; one of said rotary members has a plurality of grooves or notches provided at a circumferential position of said one of said rotary members; and, said spring mechanism includes a protrusion biased against said circumferential position on said one of said rotary members in a circumferentially immobile manner and said protrusion is engaged in a corresponding one of said grooves or notches in each of said rotary positions.

5. The device of claim 1, further comprising a manually actuated input element connected to said gear assembly for imparting a torque thereto so as to cause said rotary members to rotate synchronously.

6. The device of claim 1, further comprising a power source to drive said illumination rotary member and said observation rotary member via said gear assembly to rotate synchronously among a plurality of rotary positions corresponding to respective ones of said working modes.

7. The device of claim 6, wherein said power source comprises a motor drive coupled via said gear assembly to said illumination rotary member or said observation rotary member.

8. The device of claim 7, wherein said device further comprises a sensor for detecting the rotary position of said illumination rotary member and/or said observation rotary member; and, said sensor is operatively connected to said motor drive to stop said motor drive in response to a detection by said sensor of a predetermined rotary position.

9. The device of claim 8, wherein said device further comprises a magnet provided in said illumination rotary member or in said observation rotary member; and, said sensor is a Hall sensor for detecting said predetermined rotary position when aligned with said magnet.

10. The device of claim 8, wherein said device further comprises a shade arranged in said illumination rotary member or said observation rotary member; and, wherein said sensor is a light interrupter for detecting said predetermined rotary position when aligned with said shade.

11. A surgical microscope defining an observation beam path and being operable in multiple working modes, the surgical microscope comprising:
- a device for switching said surgical microscope into and out of said working modes;
- an eyepiece or observation instrument arranged in said observation beam path;
- a light source defining an illumination beam path for irradiating an object viewable via said observation beam path;
- said device including an observation rotary member defining a first rotational axis and being arranged in said observation beam path;
- an illumination rotary member defining a second rotational axis transverse to said first rotational axis and being arranged in said illumination beam path;
- a gear assembly connecting said rotary members directly to each other so as to permit said rotary members to rotate synchronously among a plurality of rotary positions corresponding to respective ones of said working modes;
- said illumination rotary member having a plurality of first light-through-portions for passing light at each of said rotary positions from said light source through one or more of said first light-through-portions along said illumination beam path to irradiate onto said object; and,
- said observation rotary member having a plurality of second light-through-portions for passing said light irradiated on said object along said observation beam path through one or more of said second light-through-portions to arrive at said eyepiece or observation instrument.

12. The surgical microscope of claim 11, wherein, in one of said multiple rotary positions, the light-through-portion of the illumination rotary member through which light passes is a hollow illumination through-hole; and, the light-through-portion of the observation rotary member through which light passes is an observation filter for caries detection.

13. The surgical microscope of claim 12, wherein said observation filter for caries detection has a transmission ratio between 20% and 35% for light with a wavelength of 500 nm to 550 nm.

14. The surgical microscope of claim 12, wherein said observation filter for caries detection has a transmission ratio greater than 50% for light with a wavelength of 500 nm to 550 nm.

15. The surgical microscope of claim 12, wherein said observation filter for caries detection has a transmission ratio greater than 70% for light with a wavelength of 500 nm to 550 nm.

16. The surgical microscope of claim 12, wherein said observation filter for caries detection has a transmission ratio greater than 90% for light with a wavelength of 600 nm to 650 nm.

17. The surgical microscope of claim 16, wherein said observation filter for caries detection has a transmission ratio greater than 90% for light with a wavelength of 620 nm.

18. The surgical microscope of claim 12, wherein said observation filter for caries detection has a transmission ratio of less than 0.1% for light with a wavelength of 380 nm to 430 nm.

19. The surgical microscope of claim 12, wherein said observation filter for caries detection has a transmission ratio of less than 0.01% for light with a wavelength of 380 nm to 430 nm.

20. The surgical microscope of claim 12, wherein said observation filter for caries detection is a filter that is able to pass red fluorescent light therethrough.

21. The surgical microscope of claim 12, further comprising a magnification changer disposed between said illumination rotary member and said observation rotary member; and, wherein light enters the observation beam path from the illumination beam path via said magnification changer.

22. The surgical microscope of claim 12, wherein said surgical microscope is a dental surgical microscope.

23. The surgical microscope of claim 11, wherein, in one of said multiple rotary positions, the light-through-portion of the illumination rotary member through which light passes is a first polarizer as the illumination filter; and, the light-through-portion of the observation rotary member through which light passes is a second polarizer as the observation filter, the first and second polarizers having polarization directions which mutually intersect.

24. The surgical microscope of claim 23, wherein said polarization directions of the first and second polarizers are perpendicular to each other.

25. The surgical microscope of claim 11, wherein, in one of the multiple rotary positions, the light-through-portion of the illumination rotary member through which light passes is an illumination filter for extending solidifying time of a teeth filling material; and, the light-through-portion of the observation rotary member through which light passes is a hollow observation through-hole.

26. The surgical microscope of claim 25, wherein said illumination filter for extending solidifying time of the teeth filling material has a transmission ratio of greater than 90% for light having a wavelength greater than a predetermined value between 500 nm and 600 nm.

27. The surgical microscope of claim 26, wherein said wavelength lying in said range of 500 nm to 600 nm is 550 nm.

28. The surgical microscope of claim 25, wherein the illumination filter for extending solidifying time of a teeth filling material is a filter that is able to filter out part or all of UV light and/or blue light.

29. The surgical microscope of claim 11, wherein, in one of the multiple rotary positions, the light-through-portion of the illumination rotary member through which light passes is an illumination filter for increasing contrast for blood observation; and, the light-through-portion of the observation rotary member through which light passes is a hollow observation through-hole.

30. The surgical microscope of claim 29, wherein the filter for increasing contrast for blood observation is a green filter.

31. The surgical microscope of claim 29, wherein the filter for increasing contrast for blood observation has a higher transmission ratio for light with a wavelength between 500 nm and 550 nm than that for light with other wavelengths wherein a full width at half maximum is between +/−50 nm and +/−90 nm.

32. The surgical microscope of claim 31, wherein the wavelength between 500 nm and 550 nm is 525 nm.

33. The surgical microscope of claim 31, wherein said full width at half maximum is +/−70 nm.

34. The surgical microscope of claim 11, wherein, in one of the multiple rotary positions, the light-through-portion of the observation rotary member through which light passes is an observation filter for increasing contrast for blood observation; and, the light-through-portion of the illumination rotary member through which light passes is a hollow illumination through-hole.

35. The surgical microscope of claim 11, wherein said light source has a central wavelength of between 500 nm and 550 nm in a working mode of increasing contrast for blood observation.

36. The surgical microscope of claim 35, wherein said central wavelength is 525 nm.

37. The surgical microscope of claim 11, further comprising a manually actuated input element connected to said gear assembly for imparting a torque thereto so as to cause said rotary members to rotate synchronously.

38. The surgical microscope of claim 11, further comprising a power source to drive said illumination rotary member and said observation rotary member via said gear assembly to rotate synchronously among a plurality of rotary positions corresponding to respective ones of said working modes.

39. A device for switching a surgical microscope into and out of multiple working modes, the surgical microscope defining an observation beam path and having a light source defining an illumination beam path for irradiating an object viewable via said observation beam path, said surgical microscope further having an eyepiece or observation instrument arranged in said observation beam path, said device comprising:

an observation rotary member defining a first rotational axis and being arranged in said observation beam path;

an illumination rotary member defining a second rotational axis transverse to said first rotational axis and being arranged in said illumination beam path;

a gear assembly connecting said rotary members directly to each other so as to permit said rotary members to rotate synchronously among a plurality of rotary positions corresponding to respective ones of said working modes;

said illumination rotary member having a plurality of first light-through-portions for passing light at each of said rotary positions from said light source through one or more of said first light-through-portions along said illumination beam path to irradiate onto said object;

said observation rotary member having a plurality of second light-through-portions for passing said light irradiated on said object along said observation beam path through one or more of said second light-through-portions to arrive at said eyepiece or observation instrument;

said illumination rotary member and said observation rotary member being respective discs having respective peripheries;

said gear assembly including said discs being configured to have respective sets of teeth on corresponding ones of said peripheries;

said sets of teeth being mutually meshed to permit the synchronous rotation thereof;

a power source to drive said illumination rotary member and said observation rotary member via said gear assembly to rotate synchronously among a plurality of rotary positions corresponding to respective ones of said working modes; and, said power source including a motor drive coupled via said gear assembly to said illumination rotary member or said observation rotary member.

\* \* \* \* \*

UNITED STATES PATENT AND TRADEMARK OFFICE
CERTIFICATE OF CORRECTION

PATENT NO. : 11,054,623 B2
APPLICATION NO. : 15/845782
DATED : July 6, 2021
INVENTOR(S) : T. Ma et al.

Page 1 of 1

It is certified that error appears in the above-identified patent and that said Letters Patent is hereby corrected as shown below:

In the Specification

<u>In Column 12:</u>
Line 45: delete "A" and substitute -- $\lambda$ -- therefor.

<u>In Column 13:</u>
Line 2: delete "A" and substitute -- $\lambda$ -- therefor.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*